US009504404B1

(12) United States Patent
Shao et al.

(10) Patent No.: US 9,504,404 B1
(45) Date of Patent: Nov. 29, 2016

(54) ANTIPODAL VIVALDI ANTENNA ARRAY FOR BIOMEDICAL IMAGING

(71) Applicant: The University of North Carolina at Charlotte, Charlotte, NC (US)

(72) Inventors: Wenyi Shao, Alexandria, VA (US); Ryan S. Adams, Harrisburg, NC (US)

(73) Assignee: THE UNIVERSITY OF NORTH CAROLINA AT CHARLOTTE, Charlotte, NC (US)

( * ) Notice: Subject to any disclaimer, the term of this patent is extended or adjusted under 35 U.S.C. 154(b) by 487 days.

(21) Appl. No.: 14/054,105

(22) Filed: Oct. 15, 2013

Related U.S. Application Data (60) Provisional application No. 61/853,673, filed on Apr. 10, 2013.

(51) Int. Cl.
| | | |
|---|---|---|
| *A61B 5/05* | (2006.01) | |
| *H01Q 21/06* | (2006.01) | |
| *G01S 13/88* | (2006.01) | |
| *G01S 13/89* | (2006.01) | |
| *H01Q 13/08* | (2006.01) | |

(52) U.S. Cl.
CPC ........... *A61B 5/0507* (2013.01); *G01S 13/887* (2013.01); *G01S 13/89* (2013.01); *H01Q 13/085* (2013.01); *H01Q 21/064* (2013.01)

(58) Field of Classification Search
CPC ... G01S 13/887; G01S 13/89; H01Q 21/064; H01Q 13/085
See application file for complete search history.

(56) References Cited

U.S. PATENT DOCUMENTS

| | | | | |
|---|---|---|---|---|
| 5,841,288 A | * | 11/1998 | Meaney | G01N 22/00 324/637 |
| 6,175,768 B1 | | 1/2001 | Arndt et al. | |
| 7,746,266 B2 | * | 6/2010 | Zoughi | G01S 7/025 342/179 |
| 8,089,417 B2 | | 1/2012 | Popovic et al. | |
| 8,207,733 B2 | | 6/2012 | Meaney et al. | |
| 2008/0211726 A1 | | 9/2008 | Elsallal et al. | |
| 2009/0015832 A1 | * | 1/2009 | Popovic | A61B 5/05 356/342 |
| 2009/0027288 A1 | | 1/2009 | Lee et al. | |
| 2010/0145190 A1 | | 6/2010 | Bourqui et al. | |
| 2012/0330151 A1 | * | 12/2012 | Weinstein | A61B 8/085 600/427 |

(Continued)

OTHER PUBLICATIONS

Xiaodong Zhuge et al., Circularly Tapered Antipodal Vivaldi Antenna for Array-Based Ultra-Wideband Near-Field Imaging, Proceedings of the 6$^{th}$ European Radar Conference, 2009, pp. 250-253.

(Continued)

*Primary Examiner* — Katherine Fernandez
*Assistant Examiner* — Colin T Sakamoto
(74) *Attorney, Agent, or Firm* — Foley & Lardner LLP (57) ABSTRACT

A high-performance, broad-band antenna that is small enough to be used in an array for biomedical imaging, yet has an aperture large enough to allow operations in the 1 GHz to 2.7 GHz frequency range. The present antenna advantageously uses a Vivaldi antenna with unique lobe designs to provide a small antenna that provides excellent near field imaging. The ends of each lobe have a tilted half-disc shape that increases the aperture of the antenna without increasing overall size. Other unique features of the lobes include exponential structures and an impedance matching design. Multiple units of the present antipodal Vivaldi antenna can be used in an array of antennas. Such an array, or stack or multiple arrays, can be used in many microwave applications for biomedical imaging.

15 Claims, 10 Drawing Sheets

(56) References Cited

U.S. PATENT DOCUMENTS

| | | | |
|---|---|---|---|
| 2013/0018591 A1 | 1/2013 | Grzegorczyk | |
| 2014/0155740 A1* | 6/2014 | Semenov | A61B 5/0073 600/425 |
| 2014/0218230 A1* | 8/2014 | Ostadrahimi | G01N 22/00 342/179 |

OTHER PUBLICATIONS

Beibei Zhou et al., UWB Microwave Imaging for Early Breast Cancer Detection: Effect of the Coupling Medium on Resolution, IEEE, 2004, pp. 431-434.

Jeremie Bourqui et al., Balanced Antipodal Vivaldi Antenna With Dielectric Director for Near-Field Microwave Imaging, IEEE Transactions on Antennas and Propagation, vol. 58, No. 7, Jul. 2010, pp. 2318-2326.

M. O'Halloran et al., Rotating Antenna Microwave Imaging System for Breast Cancer Detection, Progress in Electromagnetics Research, vol. 107, 2010, pp. 203-217.

Aaron Zachary Hood et al., A Small Antipodal Vivaldi Antenna for Ultrawide-Band Applications, IEEE Antennas and Wireless Propagation Letters, vol. 7, 2008, pp. 656-660.

Wenyi Shao et al., UWB Imaging with Multi-Polarized Signals for Early Breast Cancer Detection, IEEE, 2010, 4 pages.

W. Shao et al., Multi-Polarized Microwave Power Imaging Algorithm for Early Breast Cancer Detection, Progress in Electromagnetics Research M, vol. 23, 2012, pp. 93-107.

Wenyi Shao et al., Two Antipodal Vivaldi Antennas and an Antenna Array for Microwave Early Breast Cancer Detection, Microwave and Optical Technology Letters, vol. 55, No. 3, Mar. 2013, pp. 670-674.

U.S. Appl. No. 15/094,368, filed Apr. 8, 2016, Ellumen, Inc.

U.S. Appl. No. 15/177,511, filed Jun. 9, 2016, Ellumen, Inc.

\* cited by examiner

Electric Field of Antenna Unit (6GHz)

Fig. 6B

Electric Field of Antenna Unit (10GHz)

ANTIPODAL VIVALDI ANTENNA ARRAY FOR BIOMEDICAL IMAGING

This application claims priority to U.S. Provisional Application No. 61/853,673, filed Apr. 10, 2013, whose entire contents are incorporated herein by reference.

BACKGROUND OF THE INVENTION

The present invention relates generally to the field of microwave imaging, and more specifically to an improved antenna design for microwave imaging of the human body.

Microwave imaging systems have found use in detection applications including determining the presence and location of unseen objects based on the reflections of microwave radiation. Microwave imaging systems illuminate a target, such as a part of the human body, having specific dielectric properties, with electromagnetic (EM) waves, which penetrate the target and interact with the interior. The waves are then reflected back from objects within the target and their properties are monitored to determine presence and location information. Most dielectric materials such as clothing, paper, and plastic are nearly transparent over the spectral band of microwave radiation, thus microwave imaging have proven to be beneficial in a variety of applications including security inspection systems. Perhaps most appealing is the fact that microwaves are nonionizing at moderate power levels. Thus microwave radiation has the distinct advantage over other sources of radiation of not posing a health risk to human patients. As a result, microwaves appear well suited to biological sensing applications including early detection of breast cancer. Microwave imaging overcomes several limitations of other early-stage breast cancer detection systems such as Magnetic Resonance Imaging (MRI) and X-ray mammography that expose patients to low levels of ionizing radiation. Mammography is also uncomfortable for patients as breast compression is required to reduce image blurring and to create tissue uniformity. At microwave frequencies, however, a significant dielectric contrast between normal and malignant tissue is found. Typical breast tissue, for instance, has a relative dielectric constant of about 10, while a malignant tumor has a relative dielectric constant in the range of 45-55. This results in less attenuation and reflection from the normal tissue than from malignant tissues. Malignant tumors will create microwave scattering cross-sections much larger than that of normal breast tissue of the same size. Further, healthy, fatty tissues are relatively translucent to microwaves since attenuation in normal breast tissue is low enough to make signal propagation through even large breast volumes quite feasible. Microwave imaging is therefore a safe, comfortable, and accurate method for the early detection of breast cancer.

SUMMARY OF THE INVENTION

A number of attempts have been made at providing a microwave antenna design for microwave imaging applications. However, these antennas have various drawbacks including their large size, small apertures, inability to operate under 2.7 GHz, and non-planar structures that makes them difficult to use as a base for an antenna array, including antenna arrays with multiple layers. Operating in frequencies from 10 GHz to 26 GHz is typically of no use in medical imaging, due to insufficient penetration depth (<5 cm). In the medical imaging field, these frequencies can be viewed as a waste of radiation power and unnecessary antenna capabilities.

Antennas that are used in Bio-Medical Imaging (BMI), especially breast cancer imaging, are required to be small. Small antennas reduce the error associated with antenna position, and thus, improve the accuracy of the system. To date, only a few small broad-band antennas for medical detections have been successful. Vivaldi antennas that have been considered for imaging up to now have been too big to be reasonably applied in a multi-static breast cancer detection system wherein one antenna serves as a transmitter and many antennas serve as receivers. It has been shown that multi-static systems are able to provide better imaging results than mono-static systems in breast cancer detection. In mono-static systems, one antenna serves as the transmitter as well as the receiver.

There is a demand for a new microwave antenna design to provide nonionizing, reliable, and inexpensive detection for medical imaging. The ideal antenna could be used in a multi-static imaging system that images parts of the human body including the knee and breast, including regular early-stage-breast-cancer diagnosis. High resolution microwave tomography can be used alone in the diagnosis process or microwave imaging can be used to complement the current X-ray examination. The image quality provided by microwave imaging techniques is affected by the number and efficiency of the receivers, the synthetic aperture of the antenna array, and bandwidth of the probing signal. It is very important to obtain a high-performance, broad-band antenna that satisfies these needs.

A high-performance, broad-band antenna that is small enough to be used in an array for biomedical imaging, and that has an aperture large enough to allow operations in the 1 GHz to 2.7 GHz frequency ranges is described below. The present antenna advantageously uses a Vivaldi antenna with a unique design to provide a small antenna that provides excellent near field imaging. The present antipodal Vivaldi antenna is well suited for microwave medical imaging. To date there have been no broad-band antennas capable of employing the full spectrum of between 1.0 GHz and 10 GHz, while also being provided in a suitable small size for human tissue imaging. The present antenna and antenna arrays fill that void. Now, all of the useful information attainable between 1 GHz and 2.7 GHz is available for medical imaging applications. The present antenna's working frequency is the entire range of frequencies that are important to medical imaging, 1 GHz to 10 GHz. However, the most important operating frequencies provided by the present antenna are typically those that fall between 1 GHz and 2.7 GHz. This frequency range is very important to medical imaging as it allows for the localization of objects within human tissue that are the targets of medical examinations.

The present design allows the antenna to operate below 2.7 GHz, or in the low-edge frequencies. The ability to work in a low-edge frequency is determined by the physical end of the antenna. To extend the working frequency to a lower value, one must expand an antenna's aperture, but this usually increases the dimension of the antenna. One of our many novel features is that we use tilted half-circle, or half-disc design at the end of our terminals, or lobes. An advantage of the half-disc is to smooth the terminal, thus to reduce reflections at the end of the antenna. Another advantage of the tilted half-disc design is that the width of the aperture is increased without increasing the overall size of the antenna. A further unique feature of the present design is that our transition line is linearly reduced, when the ground plane is changing exponentially on the backside of the substrate, which maintains constant impedance.

BRIEF DESCRIPTION OF THE DRAWINGS

An embodiment will now be described in more detail with reference to the accompanying drawings, given only by way of example, in which.

DETAILED DESCRIPTION OF THE INVENTION

Figure 1A:
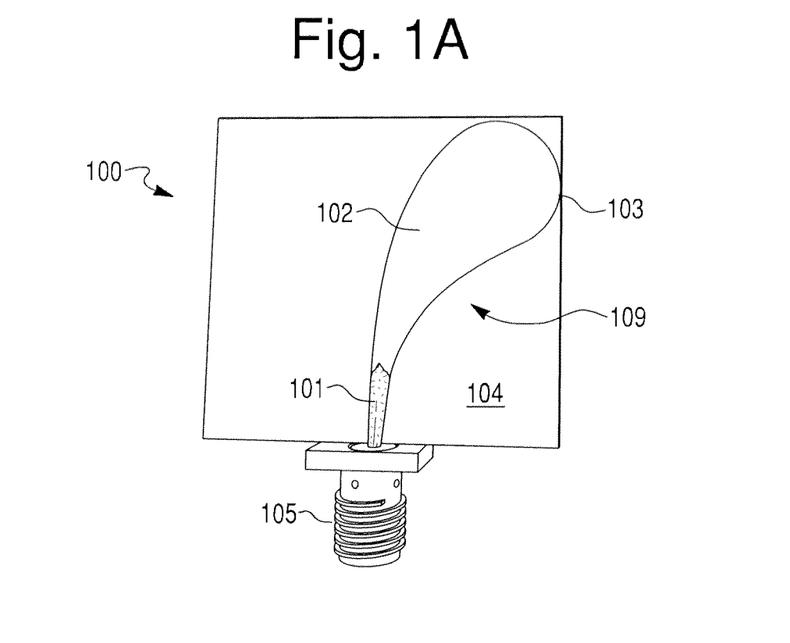
FIG. 1A shows the front side of one embodiment of the present antipodal Vivaldi antenna.

FIG. 1A shows the front side of one embodiment of the present antipodal Vivaldi antenna 100. The front side lobe 109 comprises a circularly tapered end 103 that preferably takes on a tilted half disc shape. This preferred tilted half disc shape is shown in greater detail in FIG. 8. The front side lobe 109 transitions from the circularly tapered end 103 to an exponential structure 102 wherein the width of the lobe 109 narrows exponentially to the bottom of the structure 102 The front side lobe 109 then transitions to a microstrip 101. The microstrip 101 is connected to a coupling device 105 that connects the microstrip 101 to the source feeds from the microwave imaging system, shown in FIG. 13. The coupling device 105 is preferably a SMA connector. The front side lobe 109 is placed on the front side of a substrate 104. The substrate 104 is preferably constructed using TMM 10 from the Rogers Corporation, and has a thickness of 1.27 mm, and a relative permittivity of 9.2.

Figure 1B:
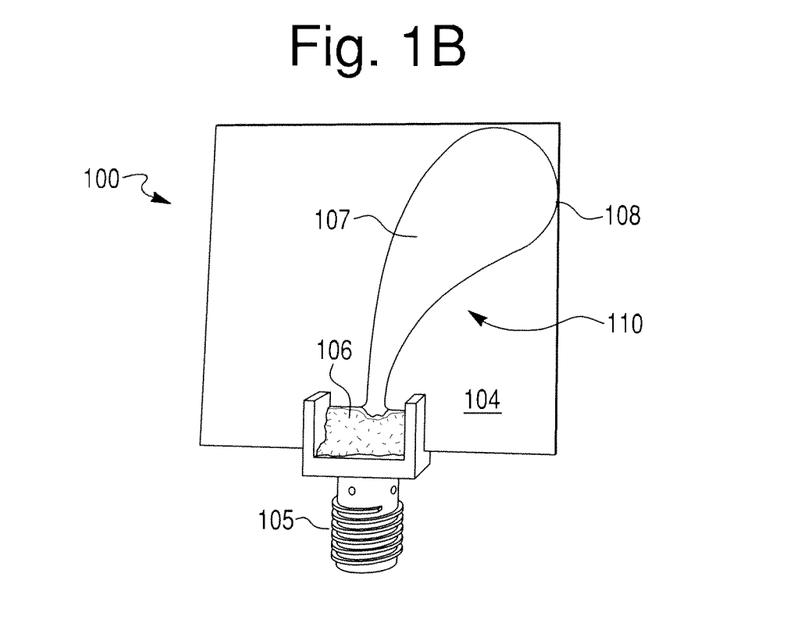
FIG. 1B shows the back side of one embodiment of the present antipodal Vivaldi antenna.

FIG. 1B shows the back side of one embodiment of the present antipodal Vivaldi antenna 100. The back side lobe 110 is placed on the back side of the substrate 104. The back side lobe 110 comprises circularly tapered end 108 that preferably takes on a tilted half disc shape (shown in greater detail in FIG. 8). The back side lobe 110 transitions from the circularly tapered end 108 to an exponential structure 107 wherein the width of the lobe 110 narrows exponentially as it approaches the bottom of the structure 107, where the lobe 110 connects to the ground plane 106 and the coupling device 105.

Figure 2A:
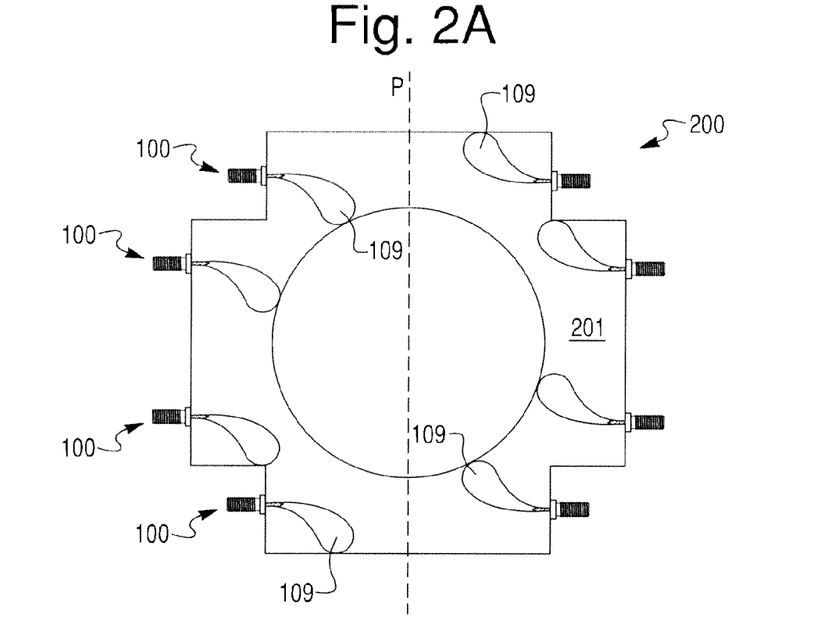
FIG. 2A shows the front side (top view) of one embodiment of the present antipodal Vivaldi antenna array.

FIG. 2A shows the front side of one embodiment of the present antipodal Vivaldi antenna array 200. The antenna array 200 comprises eight of the present antipodal Vivaldi antennas 100 with four antenna elements on the left side of a notched substrate 201 and four antenna elements on the right side of the notched substrate 201. The four antennas 100 on the left side of the substrate 201 are positioned so that their coupling feeds point toward the left, and the four antennas on the right side of the substrate 201 are positioned so that their coupling feeds point toward the right. The front side of the antenna array 200 includes eight front side lobes 109 from the eight antenna elements. The arrangement of the antennas 100 in the array 200 makes each antenna element easy to feed when the array is installed in an imaging system. The hole in the middle of the substrate 201 allows for easy and precise measurement of a breast, or a knee. Antennas with holes of various radii can be provided so as to allow for specific patient's requirements. Having all the antennas 100 on a single substrate 201 makes their relative positions fixed, thereby easing the burden on system calibrations before each examination, and reducing the chance of measurement errors. Again, the substrate 201 is preferably made of TMM 10 from the Rogers Corporation, has a thickness of 1.27 mm, and a relative permittivity of 9.2.

Figure 2B:
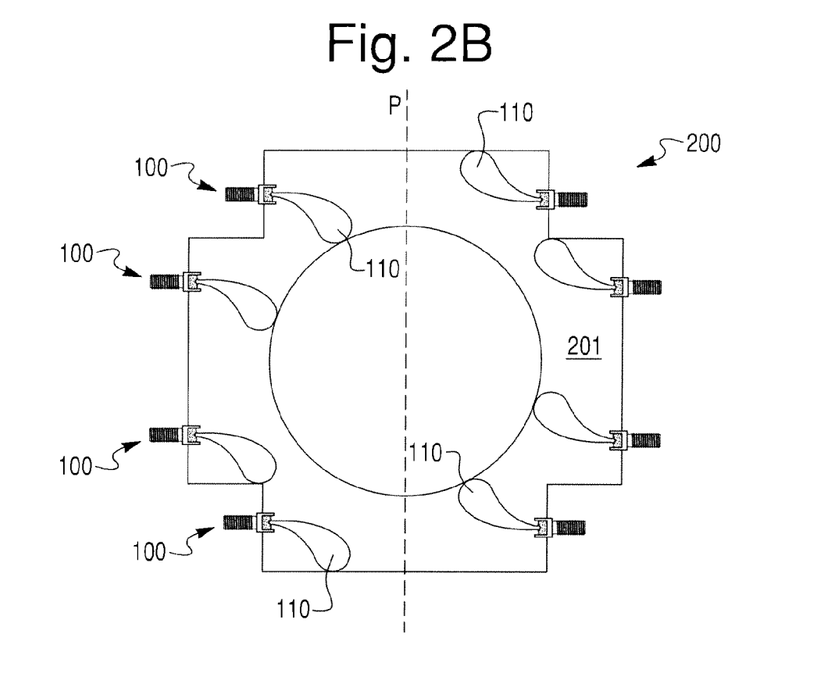
FIG. 2B shows the back side (bottom view) of one embodiment of the present antipodal Vivaldi antenna array.

FIG. 2B shows the back side of the present antipodal Vivaldi antenna array 200. The antenna array 200 shows the eight antipodal Vivaldi antennas 100 having the same basic arrangement as the front side, with four antenna elements on the left side of the notched substrate 201 and four antenna elements on the right side of the notched substrate 201. The four antennas 100 on the left side of the substrate 201 are positioned so that their coupling feeds point to the left, and the four antennas on the right side of the substrate 201 are positioned so that their coupling feeds point to the right, for easy installation in an imaging system. The back side of the antenna array 200 includes eight back side lobes 110 from the eight antenna elements.

The polarization of radiation from all of the lobes 109 and 110 in FIGS. 2A and 2B, is along line P. As discussed below, by rotating the array 200 clockwise or counter-clockwise (in FIGS. 2A and 2B) the polarization can be changed, which allows collecting more data, and improves image quality.

The present array 200 preferably operates in the multi-static mode, wherein the transmitter is located at a different location than the multiple receivers. Each of the antennas 100 in the array 200 can be employed as a transmitter or a receiver in a multi-static imaging system. Because of the small size of the present antenna 100 such an array is possible. As shown in FIG. 2B, eight antennas 100 are designed to be on one substrate 201 and have the same polarization. The overall size of this embodiment of the antipodal Vivaldi antenna array 200 is 152.4×152.4×1.27 mm$^3$.

Figure 3A:
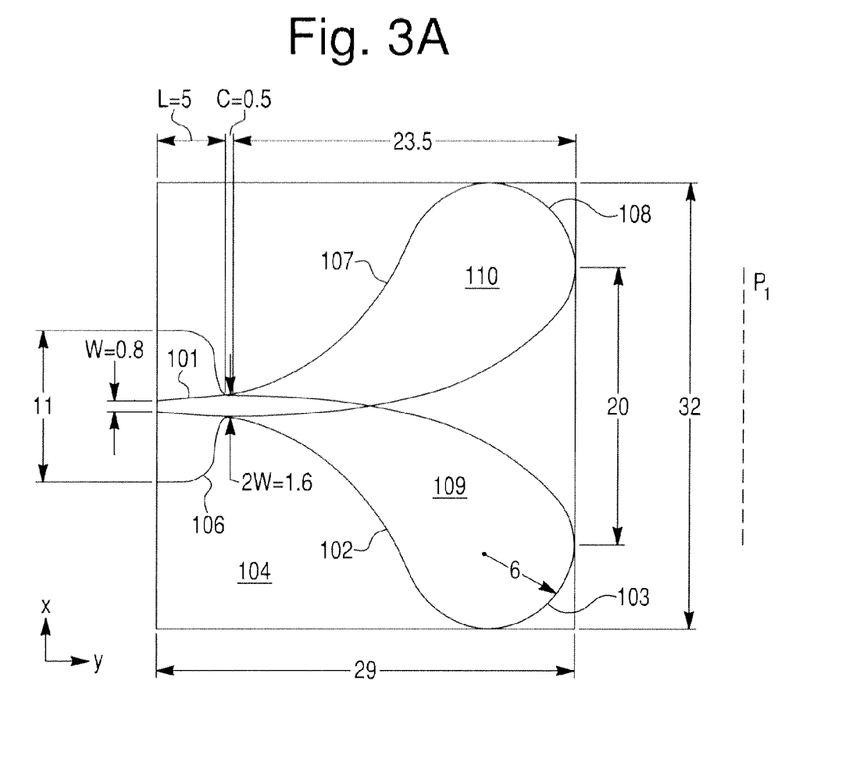
FIG. 3A is a schematic of an embodiment of the present antenna mounted on a see-through substrate.

FIG. 3A is a schematic of an embodiment of the present antenna mounted on a substrate 104 that is see-through. Both front side lobe 109 and back side lobe 110 are visible. The microstrip 101 transitions to a parallel strips transmission line. Along the transition, the conductor width increases linearly while the ground width decreases exponentially to retain constant impedance, such that reflections on the transitions are reduced. The parallel strips transmission line extends for a short distance before the front and back side lobes 103 and 108, which act as conductors, start to flare in opposite directions with exponential curves to create an antenna aperture of 20 mm.

The present antipodal Vivaldi antennas have exponential structures 102 and 107. FIG. 3A presents the geometry and parameter values of an embodiment of the present antenna. The inner and outer curvatures of the antenna (inner curves form the gap) are defined by:

$$x_{in} = c_1[e^{c_2(y-L-C)} - 1] - W \quad (1)$$

$$x_{out} = W\left(2e^{\frac{y-L-C}{6}} - 1\right) \quad (2)$$

where W, L, and C are shown in FIG. 3A. The coefficients for the antenna are c1=0.25 and c2=0.15.

The 20 mm aperture is important, as it allows the antenna to operate under 2.7 GHz. Other important dimensions in FIG. 3A are W and 2W. These two dimensions describe the widths of the microstrip 101 with 2W being the width at the top and W being the width at the bottom of the microstrip. The present microstrip 101 advantageously tapers down linearly. The front side end 103 and back side end 108 are illustrated with exemplary distances between the ends. All distances are in millimeters (mm).

The polarization of radiation from the antenna in FIG. 3A is along line $P_1$ (in the same direction as if a dipole were placed parallel to $P_1$).

Figure 3B:
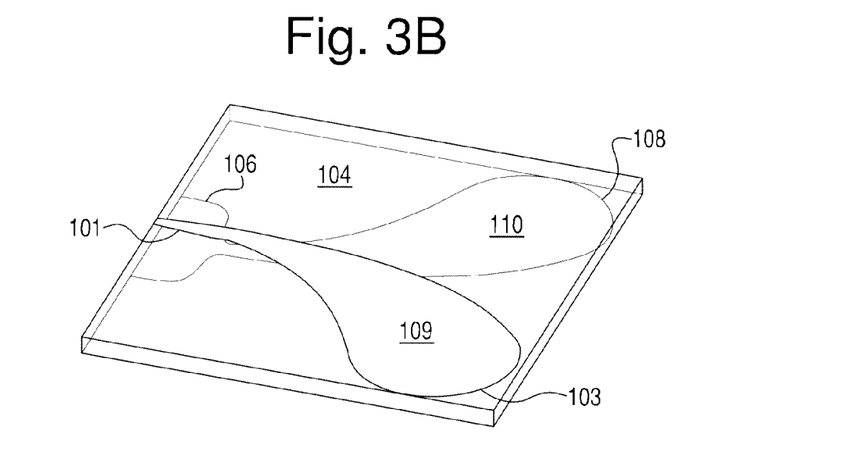
FIG. 3B is a perspective view showing a 3-D image of one embodiment of the present antenna mounted on the see-through substrate.

FIG. 3B provides a 3-D image of the present antenna mounted on a substrate 104 that is see-through. The geometry of the microstrip 101 and the ground plane 106 are easily seen in the figure. The geometry and separation of the front lobe 103 and back side lobe 108 also well illustrated in the figure.

Figure 4:
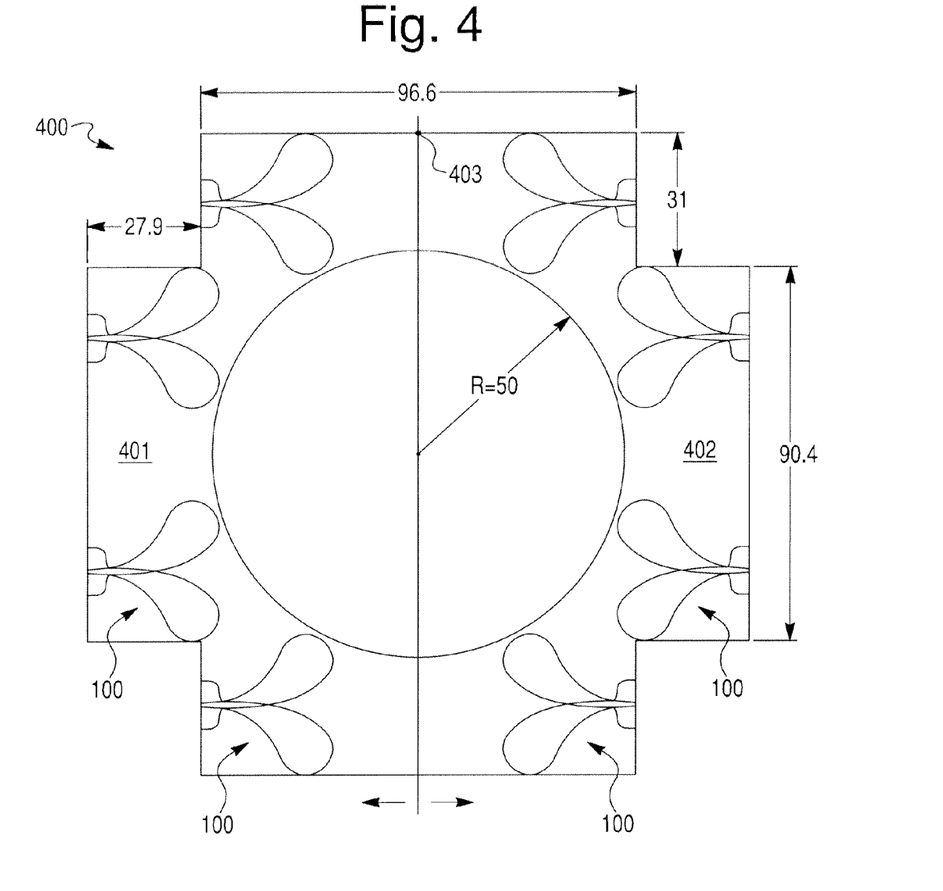
FIG. 4 shows an alternate embodiment of the present antipodal Vivaldi antenna array.

FIG. 4 shows an alternate embodiment of the antipodal Vivaldi antenna array 400. In this embodiment, the array 400 is provided in two halves 401 and 402 that may be completely separate from each other, or may be connected via a swivel point 403. This alternative embodiment is specifically designed for knee examinations and avoids the need for the patient to step through the center hole in the design shown in FIGS. 2A and 2B. The swivel point 403 allows the two halves of the array to open and close in a clamshell fashion. Once in the open position, the patient places his leg in the center of the array 400, and the two halves are moved to the closed position. After all necessary image data has been captured, the array 400 is re-opened and the patient removes his leg. Of course, multiple arrays 400 can be stacked and used with an open-able frame to provide an increased imaging area.

In FIG. 4, the hole is shown as a circle with a 50 mm radius. However, many other shapes and dimensions are possible depending on the object being imaged.

Figure 5:
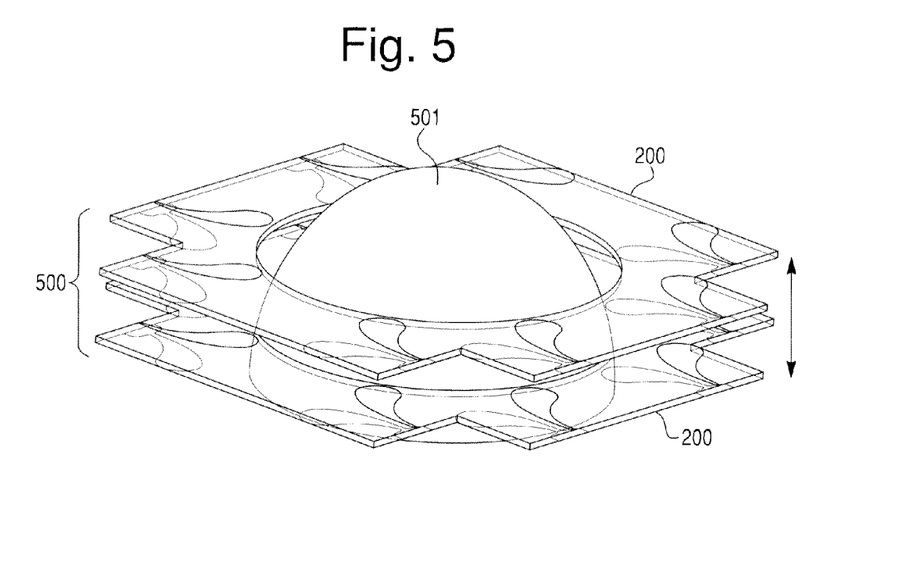
FIG. 5 shows a stack of antenna arrays that can be used for imaging a breast.

FIG. 5 shows a stack 500 of antenna arrays 200 that can be used for imaging objects inside a breast 501. The stack 500 can be provided as an aperture in an examination table that the patient lays on, and positions their breasts inside the aperture. The stack can be fixed or moveable. In a moveable embodiment, the stack 500 is attached to a moveable rail system via a frame that holds each array 200 and provides for attachment of feed lines. The stack 500 can then be moved upward and downward for targeted image acquisition. Such a moveable embodiment is also useful in examinations of the leg and knee, and of the arm and elbow.

Figure 6A:
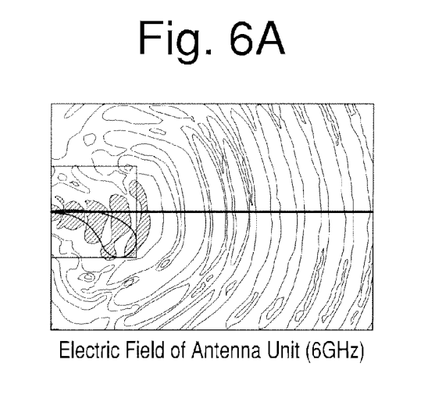
FIG. 6A shows a 2-D image of an electric field of one embodiment of the present antenna at 6 GHz.

FIG. 6A shows a 2-D image of an electric field of an embodiment of the present antenna in the X-Y plane when the frequency is 6 GHz. FIG. 6A shows the electric field generated by the present antenna has very good near-field radiation.

Figure 6B:
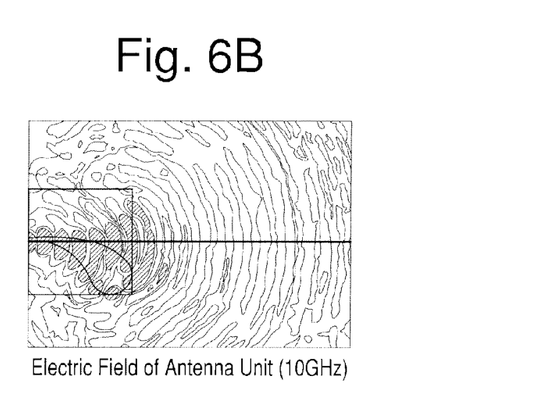
FIG. 6B shows a 2-D image of an electric field of one embodiment of the present antenna at 10 GHz.

FIG. 6B shows a 2-D image of an electric field of an embodiment of the present antenna in the X-Y plane when the frequency is 10 GHz. FIG. 6B also shows the electric field generated by the present antenna has very good near-field radiation.

Figure 7A:
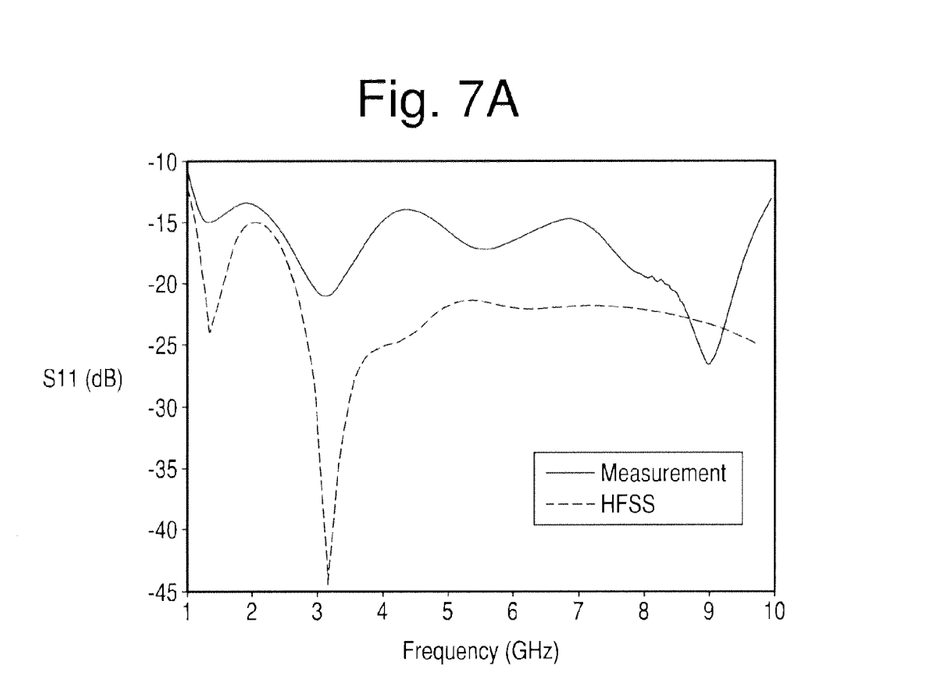
FIG. 7A shows the measured and simulated S11 for one embodiment of the present antipodal Vivaldi antenna.

FIG. 7A shows the measured and simulated S11 for an embodiment of the present antipodal Vivaldi antenna. The measurement matches the main features of the simulation, especially in the low frequency range (1 GHz to 27 GHz). The S11 values shown in FIG. 7A provide a positive indication of the present antenna's effectiveness from 1 GHz to 2.7 GHz.

Figure 7B:
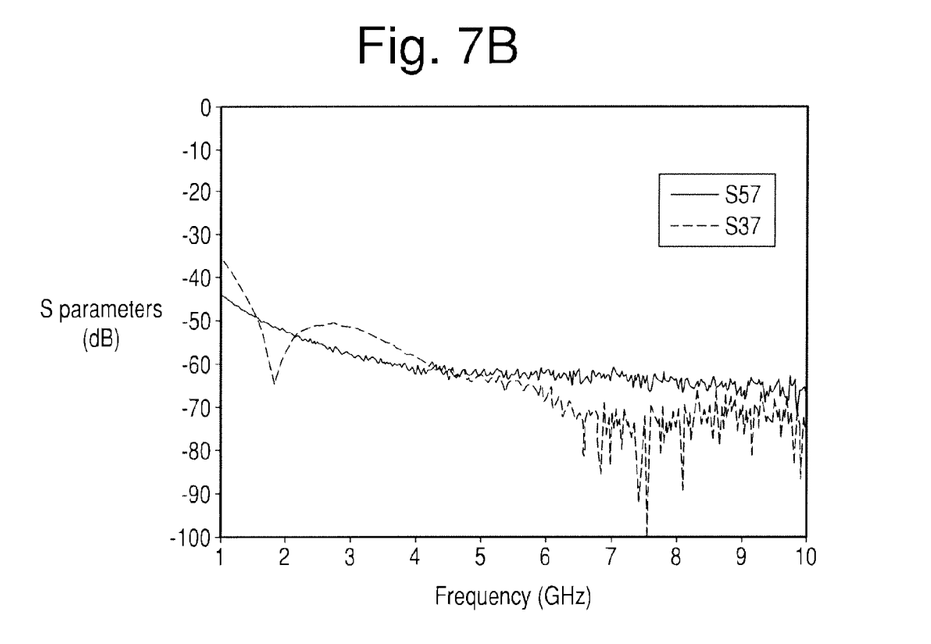
FIG. 7B shows measured S37 and S57 for elements of one embodiment of the present antipodal Vivaldi antenna array.

FIG. 7B shows measured S37 and S57 for elements of the present antipodal Vivaldi antenna array. Very weak couplings are observed between each pair of elements in the array. Because of symmetry, only S37 and S57 are illustrated in FIG. 7B, as the highest correlation can only exist in these two pairs.

Figure 8:
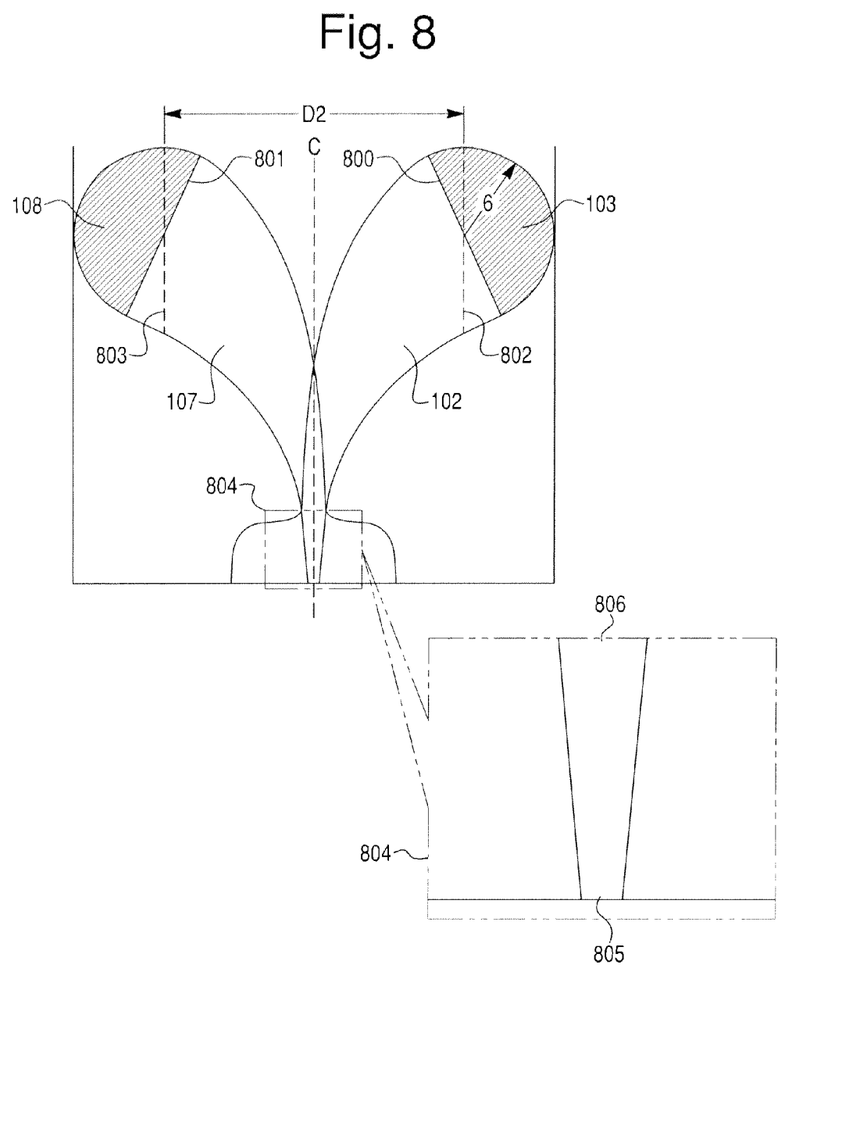
FIG. 8 illustrates the tilted half-disc design and dimensions of one preferred embodiment of the present antipodal Vivaldi antenna.

FIG. 8 illustrates the design and some dimensions of one preferred embodiment of the present antipodal Vivaldi antenna element, which are specifically designed for low-edge frequencies (1 to 2 GHz). The ability to work with low-edge frequencies is determined by the antenna's physical end. Working with these low values requires that an antenna's aperture be increased. However, this usually increases the dimensions of the antenna, something that needs to be avoided for biomedical imaging applications. One of our novel features is a titled half-circle, or half-disc, design that is used at the end of our conductors (lobes). This tilted half-disc design provides a smooth end to the conductors, thereby reducing reflections at the end of the antenna, and increases the width of the aperture without increasing the size of the antenna. The end of the front side lobe is a tilted half-disc 103, and the end of the back side lobe is another titled half-disc 108. The flat side of the half-disc 103 is illustrated by line 800. The tilting of the half-disc 103 is illustrated by the difference between line 800 and line 802. Line 802 is a vertical line parallel to centerline C of the antenna. The curvature (or the 2nd derivative) of the inner curve at the connection point between the half-disc 103 and the exponential structure 102 is 0.1644, which is equivalent to a circle having a radius of 6 mm. Thus a half circle having radius of 6 mm is attached to the end of the exponential structure 102. This curvature allows the two antenna parts (103 and 102) to have a very smooth connection. It is this smoothing of the connection that minimizes reflections at the end of antenna. The enlarged portion of FIG. 8 shows a microstrip with one end 805 connected to the feed and another end 806 connected to exponential structure 102.

The flat side of the half-disc 108 is illustrated by line 801. The tilting of the half-disc 108 is illustrated by the difference between line 801 and line 803. Line 803 is another vertical line parallel to centerline C of the antenna. The curvature (or the 2nd derivative) of the inner curve at the connection point between the half-disc 108 and the exponential structure 107 is 0.1644, which again is equivalent to a circle having a radius of 6 mm. Thus, a half circle having radius of 6 mm is attached to the end of the exponential structure 107. The distance D2 represents the aperture of the antenna. With this tilted design, the aperture is increased, which allows use of lower frequencies, which in turn allows the collection of more information about the object and improves image quality.

Figure 9:
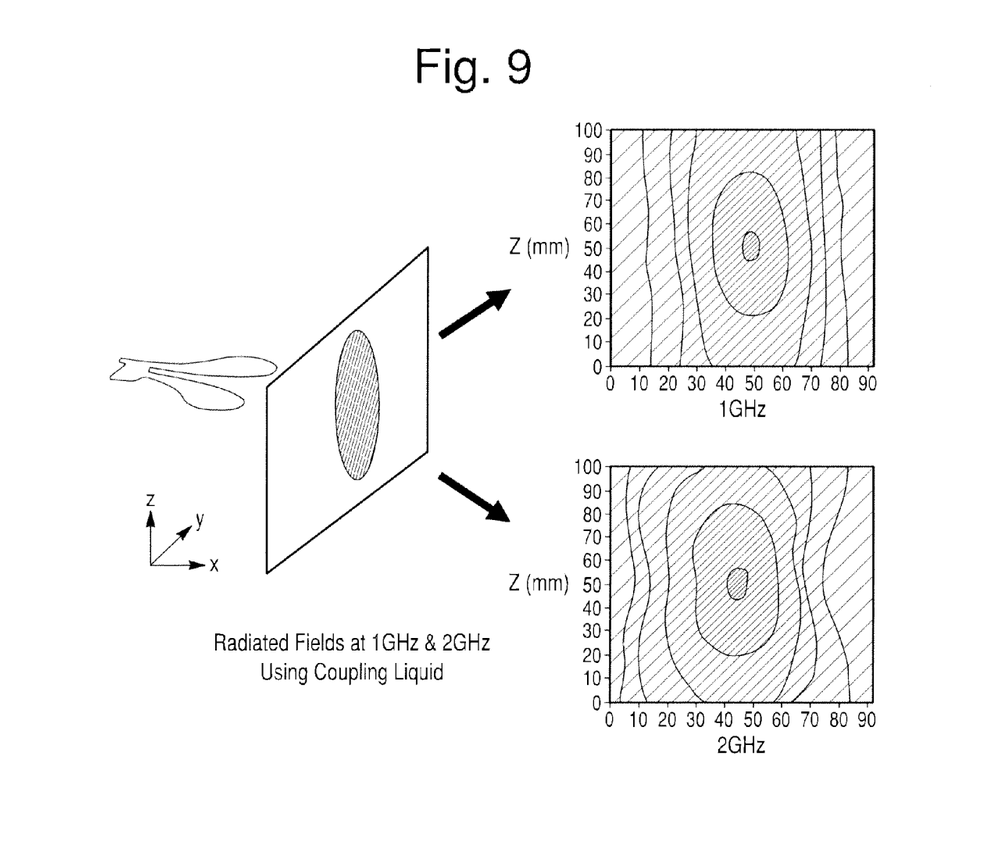
FIG. 9 shows radiated fields of one embodiment of the present antenna at 1 GHz and 2 GHz.

FIG. 9 shows radiated fields of embodiments of the present antenna at 1 GHz and 2 GHz. Each illustrated radiated field is a distance of 3 centimeter from the end of the antenna. The antenna was assumed to be immersed in the preferred coupling liquid, whose relative permittivity is 9.2, which is equal to the relative permittivity of the substrate. To verify the antenna's abilities at low frequencies, around 1 or 2 GHz, the antenna has been successfully re-simulated by FDTD. The time domain result was then converted into frequency domain through Discrete Fourier Transform.

The present antenna array has a preferred working environment. The antenna array is preferably immersed in a coupling medium. Ethanol is a commonly used medical solution that is accepted by patients, and is inexpensive. Its dielectric properties have been recently studied by several research groups. The dielectric constant is approximately 24.3-5.5, conductivity 0.7-2.7 S/m, during 1-9 GHz spectrum. So ethanol's dielectric constant is very suitable for it being a coupling medium. However, the conductivity is fairly high. To reduce the conductivity, we mixed ethanol with commercial gasoline, in a low percentage such as 10%-15%. Commercial gasoline has a lower dielectric constant, on the order of one magnitude smaller, and lower conductivity values, several orders of magnitude smaller, than ethanol. This mixture has less dissipation but does not change the dielectric constant, and is the preferred coupling liquid.

Figure 10:
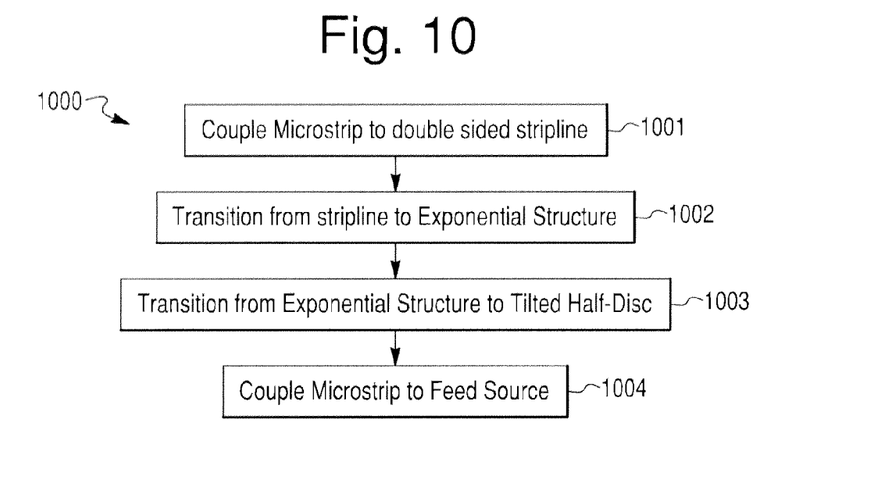
FIG. 10 is a flow chart showing exemplary steps for making one embodiment of the present antipodal Vivaldi antenna.

FIG. 10 is a flow chart 1000 showing exemplary steps for making the present antipodal Vivaldi antenna. In step 1001, the present microstrip is coupled to a stripline that extends along both sides of a substrate. In step 1002, the stripline on both sides of the substrate transition to exponential structures, wherein the width of the conductor increases exponentially. In step 1003, each conductor takes on the appearance of a lobe flaring outward, in opposite directions, and terminating in a half-disc end that is tilting downward. In step 1004, the microstrip is coupled to a feed source and transmission or reception can occur.

Figure 11:
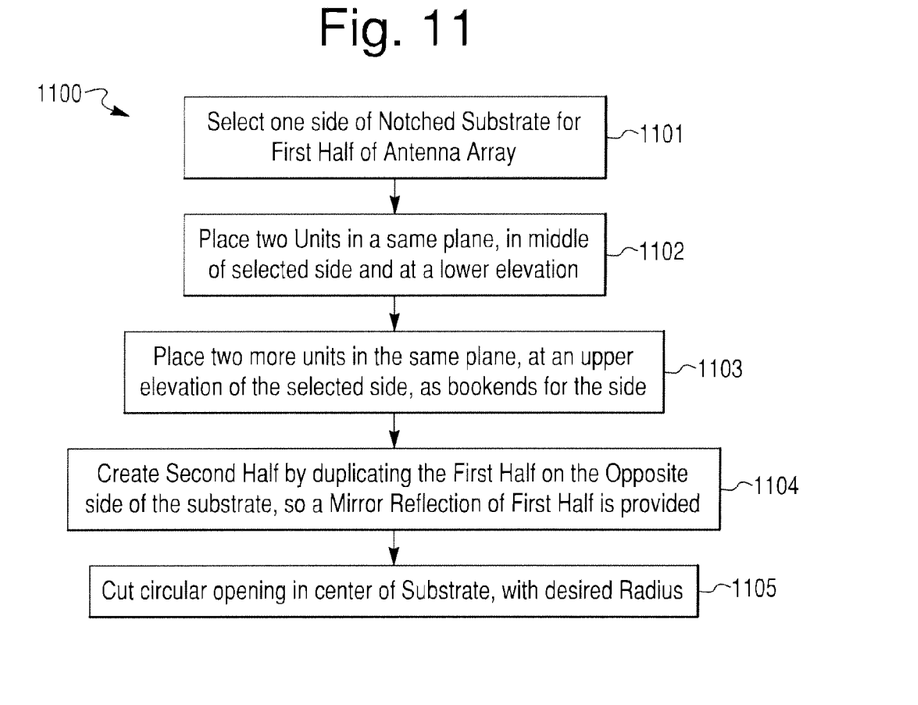
FIG. 11 is a flow chart showing exemplary steps for making one embodiment of the present antipodal Vivaldi antenna array.

FIG. 11 is a flow chart 1100 showing exemplary steps for making the present antipodal Vivaldi antenna array. In step 1101, a notched substrate is provided and one side or edge is selected for placement of the first half of the antennas in the antenna array. In the preferred embodiment, four antennas are used in each half, for a total of eight antennas in the preferred array. In step 1102, two antenna units are placed in the center of the selected side, in the middle of the side, and at the lowest elevation on the side. In step 1103, two more antenna units are placed as bookends on the selected side, in the notched positions on the substrate at the highest elevation on the selected side. In step 1104, a mirror reflection of the first half of antennas is created on the opposite side of the substrate, so that a total of eight antenna units are provided on the antenna array. In step 1105, an opening is provided in the center of the substrate for passage therethrough of body parts to be imaged. Of course, this step could be done first.

Figure 12:
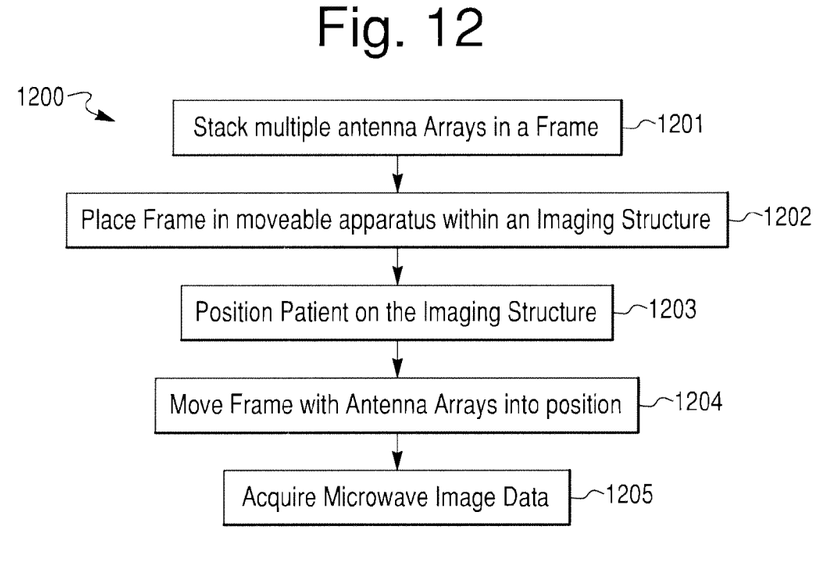
FIG. 12 is a flow chart showing exemplary steps for using one embodiment of the present antipodal Vivaldi antenna array; and, FIG. 13 shows an exemplary system that uses a stack of one embodiment of the present antipodal Vivaldi antenna arrays to acquire microwave image data.

FIG. 12 is a flow chart 1200 showing exemplary steps for using the present antipodal Vivaldi antenna array. In step 1201, a desired number of array substrates are placed into a frame that holds the substrates at desired distances away from each other. In step 1202, the frame containing the antenna arrays is placed into the moveable apparatus of an imaging structure. The imaging structure may include a chair, table or bed that is used by the patient for support during imaging. The imaging structure may also hold electronics and circuitry designed to assist in the imaging process. In step 1203, the patient positions himself on the imaging structure. In the case of a knee examination, the patient may place his leg into the center of one or more arrays, while standing, sitting or laying down. In the case of a breast examination, the patient may lay down on a table or bed, and position their breast over an aperture on the table or bed. In step 1204, the antenna array is moved into position. This can be done by a rail system, or by simply closing a clam shell designed array. If the array is statically positioned, then this step can be skipped. In step 1205, imaging data is acquired. In the preferred embodiment, the antenna arrays operate in the multi-static mode, where one of the antennas acts as the transmitter and the multiple other antennas act as the receivers. Any antenna element in the array can be employed as a transmitter in the multi-static imaging system.

Figure 13:
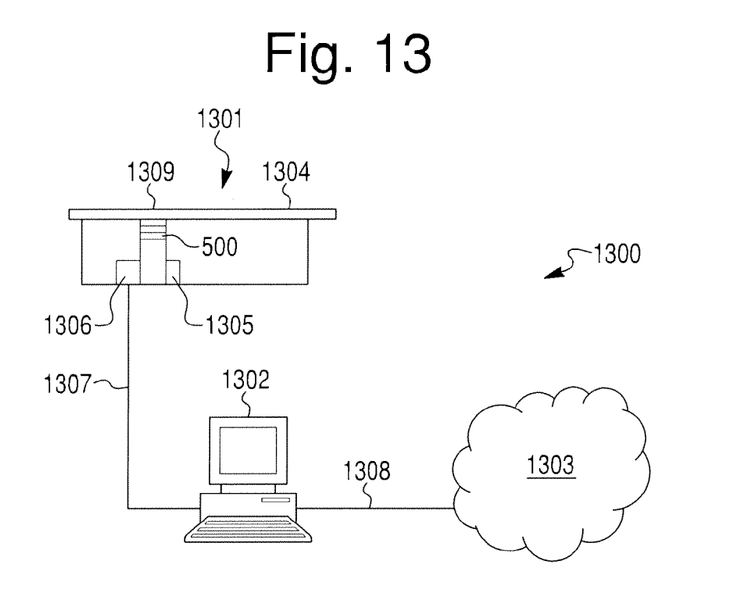

FIG. 13 shows an exemplary system 1300 that uses a stack 500 of the present antipodal Vivaldi antenna arrays to acquire biomedical microwave image data. An imaging structure 1301 is provided comprising an examination table 1304, a stack 500 of antenna arrays on a rail system or other mechanism underneath the examination table, circuitry 1305 for moving the stack of arrays upward and downward, and circuitry 1306 that provides communications (input/output) between the antenna array and an imaging computer 1302. The circuitry can generate and receive signals in the 1.0 GHz to 2.7 GHz range. The mechanism can be any type of mechanism to translate and/or rotate the antenna array, using motors, gears, or any other mechanical arrangement. This particular imaging structure 1301 is designed for imaging breasts, however, other imaging structures can be provided in other embodiments for imaging other parts of the human body. The patient lays, face down on the examination table 1304 and position's their breast over an area 1309 on the table that is directly above, or within the center of, the stack 500. Once in position, the stack is raised, if necessary, and imaging of the breast takes place. During imaging, the antenna array radiates broad-band microwave signals, and receives scattered field signals from the breast. Different frequencies may be used to collect more data regarding the electrical properties of the tissue and thus improve image quality. Also, different frequencies may be used to image different part of the body. The imaging data is sent to examination computer (or processor) 1302 programmed or otherwise configured for reconstruction and display. Additionally, the image data can also be forwarded to another computer via the Internet 1303. The source feeds for the arrays preferably come from the circuitry 1306 that is part of the imaging structure 1301. The stack 500 preferably operates in the multi-static mode, allowing any antenna element in the array to be employed as a transmitter. The examination computer 1302 is connected to the imaging structure 1301 via communications link 1307. The examination computer 1302 is also connected to the Internet 1303 via communications link 1308. Communications links 1307 and 1308 can be wired or wireless links. Additional details regarding suitable microwave image processing are set forth in U.S. patent application Ser. No. 13/798,428 filed Mar. 13, 2013, whose entire contents are incorporated herein by reference for the microwave image processing techniques and equipment described therein.

The present antenna, antenna array, and stack of antenna arrays can find use in many applications. The presented antenna array can be applied in breast cancer imaging systems. By increasing the radius of the hole in the middle of the substrate, arrays can be used for knee microwave detection. The present antennas are capable of being employed as an element in any shape of antenna arrays for any specific purpose and application.

Other advantages provided by the present antenna array include: broad band; small dimensions; easy feeding; and, easy movement. Regarding broad band, microstrip antennas are usually for narrow band. However, the present antennas cover a frequency range from 1 GHz to 10 GHz. Regarding small dimensions, the present antennas have a small size, which allows more of these antennas to be positioned around the examined object simultaneously. In regards to easy feeding, all elements on one substrate have the same polarization, but the arrangement makes them still convenient to be fed. Further, the array can be easily moved up and down, and even in rotation for the purpose of obtaining more signals and polarizations. The present array is well suited for a multi-polarization, multi-static imaging system.

The invention is not limited to the embodiments described above. Instead, many other variations of the invention are possible and depend on the particular requirements at hand. Such variations are within the scope and spirit of the invention. The invention is therefore defined with reference to the following claims.

We claim:

1. An antenna comprising:
   a conductive front side lobe that is mounted on a front side of a support, the front side lobe comprising a microstrip, a front side intermediate structure having a first end connected to the microstrip and a second end opposite to the first end, and a first tilted half-disc shaped end directly connected to the second end of the front side intermediate structure at a first connection point such that an edge of the front side intermediate structure and an edge of the first tilted half-disc shaped end have an identical curvature where the edge of the front side intermediate structure and the edge of the first tilted half-disc shaped end meet; and
   a conductive back side lobe that is mounted on a back side of the support, the back side lobe comprising a ground plane, a back side intermediate structure having a first end connected to the ground plane and a second end opposite to the first end, and a second tilted half-disc shaped end directly connected to the second end of the back side intermediate structure at a second connection point such that an edge of the back side intermediate structure and an edge of the second tilted half-disc shaped end have an identical curvature where the edge of the back side intermediate structure and the edge of the second tilted half-disc shaped end meet,
   wherein the front and back side lobes flare outward from a center line of the antenna in opposite directions,
   wherein a line joining end points of the first tilted half-disc is at a non-zero angle with respect to the center line of the antenna and a line joining end points of the second tilted half-disc is at a non-zero angle with respect to the center line of the antenna,
   wherein the edge of the front side intermediate structure with respect to the center line is exponential from the second end to the first end, and the edge of the back side intermediate structure with respect to the center line is exponential from the second end to the first end.

2. An antenna as set forth in claim 1,
   wherein a width of the microstrip changes linearly from the front side intermediate structure to a feed device.

3. An antenna as set forth in claim 1,
   wherein a width of the ground plane changes exponentially from the first end of the back side intermediate structure to a feed device.

4. An antenna system, comprising:
   an antenna including
      a conductive front side lobe that is mounted on a front side of a support, the front side lobe comprising a microstrip, a front side intermediate structure, and a first tilted half-disc shaped end, and
      a conductive back side lobe that is mounted on a back side of the support, the back side lobe comprising a ground plane, a back side intermediate structure, and a second tilted half-disc shaped end; and
   a coupling medium comprising ethanol and gasoline,
   wherein the front and back side lobes flare outward from a center line of the antenna in opposite directions,
   wherein a line joining end points of the first tilted half-disc is at a non-zero angle with respect to the center line of the antenna and a line joining end points of the second tilted half-disc is at a non-zero angle with respect to the center line of the antenna.

5. An antenna system comprising:
   a planar substrate; and
   an antenna array comprising a plurality of antennas,
   wherein the antenna array lies on the planar substrate,
   wherein each of the plurality of antennas comprises:
      a conductive front side lobe that is mounted on a front side of the planar substrate, the front side lobe comprising a microstrip, a front side intermediate structure having a first end connected to the microstrip and a second end opposite to the first end, and a first tilted half-disc shaped end directly connected to the second end of the front side intermediate structure at a first connection point such that an edge of the front side intermediate structure and an edge of the first tilted half-disc shaped end have an identical curvature where the edge of the front side intermediate structure and the edge of the first tilted half-disc shaped end meet; and
      a conductive back side lobe that is mounted on a back side of the planar substrate, the back side lobe comprising a ground plane, a back side intermediate structure having a first end connected to the ground plane and a second end opposite to the first end, and a second tilted half-disc shaped end directly connected to the second end of the back side intermediate structure at a second connection point such that an edge of the back side intermediate structure and an edge of the second tilted half-disc shaped end have an identical curvature where the edge of the back side intermediate structure and the edge of the second tilted half-disc shaped end meet,
   wherein a line joining end points of the first tilted half-disc is at a non-zero angle with respect to a center line of the antenna and a line joining end points of the second tilted half-disc is at a non-zero angle with respect to the center line of the antenna,
   wherein the edge of the front side intermediate structure with respect to the center line is exponential from the second end to the first end, and the edge of the back side intermediate structure with respect to the center line is exponential from the second end to the first end.

6. An antenna system as set forth in claim 5, wherein the plurality of antennas are arranged on two opposite sides of the substrate with opposite orientations.

7. An antenna system as set forth in claim 5, wherein the substrate comprises an opening accessible from top and bottom thereof and configured to accommodate at least a portion of a body therein.

8. An antenna system as set forth in claim 7, further comprising a processor programmed to perform microwave image reconstruction of a portion of the body using a scattered field received from the portion of the body by the antenna array.

9. An antenna system as set forth in claim 5, further comprising circuitry to generate, receive, and process signals in the range of 1.0 GHz to 2.7 GHz.

10. An antenna system as set forth in claim 5, further comprising a mechanism to rotate the planar substrate such that polarization of radiation emitted from the plurality of antennas is varied.

11. An antenna system as set forth in claim 10, further comprising a processor configured to perform multi-polarized imaging based on the varied polarization.

12. An antenna system as set forth in claim 5, further comprising a plurality of flat antenna substrates stacked vertically in a direction perpendicular to a plane of the substrates.

13. An antenna system as set forth in claim 5, wherein:
   a portion of the front side lobes flare outward in one direction and a portion of the front side lobes flare outward in an opposing direction, and
   a portion of the back side lobes flare outward in one direction and a portion of the back side lobes flare outward in an opposing direction.

14. An antenna system comprising:
   a planar substrate having a cutout in a center thereof to allow placement of a portion of a body therein;
   an antenna array comprising a plurality of antennas lying on the planar substrate around the cutout and configured to acquire measurements from the portion of the body in a plane of the planar substrate by emitting polarized radiation and receiving a scattered portion thereof;
   a mechanism configured to vary polarization of the emitted polarized radiation by rotating the planar substrate; and
   a processor programmed to perform bio-medical microwave image reconstruction of the portion of the body from measurements acquired by the antenna array of various polarizations.

15. An antenna system as set forth in claim 14, further comprising a rail system configured to move the antenna array in a direction perpendicular to a plane of the planar substrate.

* * * * *